(12) United States Patent
Old et al.

(10) Patent No.: US 7,507,817 B2
(45) Date of Patent: Mar. 24, 2009

(54) PROSTAGLANDIN PRODRUGS

(75) Inventors: David W. Old, Irvine, CA (US); Vinh X. Ngo, Huntington Beach, CA (US); Wha-Bin Im, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/938,902

(22) Filed: Nov. 13, 2007

(65) Prior Publication Data

US 2008/0167311 A1    Jul. 10, 2008

Related U.S. Application Data

(60) Provisional application No. 60/866,250, filed on Nov. 17, 2006.

(51) Int. Cl.
| | | |
|---|---|---|
| *C07D 265/30* | (2006.01) | |
| *C07D 333/02* | (2006.01) | |
| *C07D 321/00* | (2006.01) | |
| *C07D 333/32* | (2006.01) | |
| *C07D 307/00* | (2006.01) | |
| *C07D 213/04* | (2006.01) | |
| *C07D 265/28* | (2006.01) | |
| *A61K 31/535* | (2006.01) | |
| *A61K 31/335* | (2006.01) | |
| *C07C 61/00* | (2006.01) | |
| *C07C 63/36* | (2006.01) | |

(52) U.S. Cl. .......................... 544/106; 549/29; 549/62; 549/200; 549/429; 549/475; 514/183; 514/228.8; 514/231.2; 514/430; 514/438; 514/449; 514/461; 514/724; 546/1; 546/255; 544/63; 544/98; 562/400; 562/405; 562/490; 562/493

(58) Field of Classification Search ................... 544/63, 544/98, 106; 514/183, 228.8, 231.2, 430, 514/438, 449, 461, 724; 546/1, 255; 549/29, 549/62, 200, 429, 475; 562/400, 405, 490, 562/493
See application file for complete search history.

(56) References Cited

FOREIGN PATENT DOCUMENTS

| WO | WO 93/14743 A | 8/1993 |
|---|---|---|
| WO | WO 2006/076370 A | 7/2006 |

OTHER PUBLICATIONS

Resul B. et al.; "Structure-Activity Relationships of Prostaglandin Analogues As Ocular Hypotensive Agents"; Current Opinion in Therapeutic Patents, vol. 3, No. 6, 1993; pp. 785.

*Primary Examiner*—Kamal A Saeed
*Assistant Examiner*—Samantha L Shterengarts
(74) *Attorney, Agent, or Firm*—Allergan, Inc.; Martin Voet; Kevin Forrestal

(57) ABSTRACT

Novel compounds, and therapeutic methods, compositions and medicament related thereto are disclosed herein.

19 Claims, No Drawings

PROSTAGLANDIN PRODRUGS

RELATED APPLICATION

This application claims the benefit of U.S. Provisional Application Ser. No. 60/866,250, filed Nov. 17, 2006, the disclosure of which is hereby incorporated in its entirety herein by reference.

BACKGROUND

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

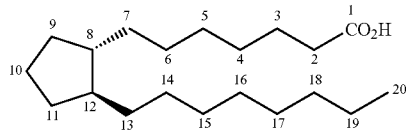

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

DESCRIPTION OF THE INVENTION

Disclosed herein is a compound comprising

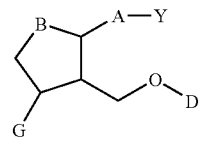

or a pharmaceutically acceptable salt thereof;

wherein Y is

—$CO_2(CH_2)_2OH$ or

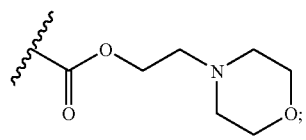

A is —$(CH_2)_6$—, cis —$CH_2CH{=}CH{-}(CH_2)_3$—, or —$CH_2C{\equiv}C{-}(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;

B is C=O, $CH_2$, CHOH, CHCl, CHF, CHBr, or CHCN;

G is OH or H; and

D is aryl or heteroaryl.

As Y is

—$CO_2(CH_2)_2OH$ or

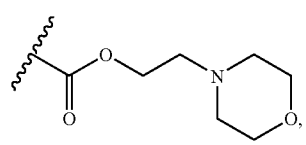

the compounds below, or salts thereof, are contemplated.

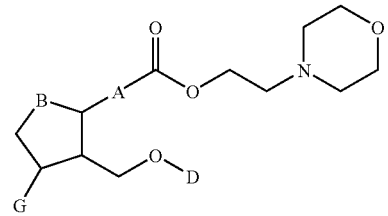

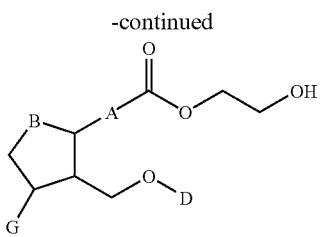

In relation to the identity of A disclosed in the chemical structures presented herein, A is —$(CH_2)_6$—, cis —$CH_2CH=CH—(CH_2)_3$—, or —$CH_2C\equiv C—(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O.

While not intending to be limiting, A may be —$(CH_2)_6$—, cis —$CH_2CH=CH—(CH_2)_3$—, or —$CH_2C\equiv C—(CH_2)_3$—.

Alternatively, A may be a group which is related to one of these three moieties in that any carbon is replaced with S or O. For example, while not intending to limit the scope of the invention in any way, A may be a moiety where S replaces one or two carbon atoms such as one of the following or the like.

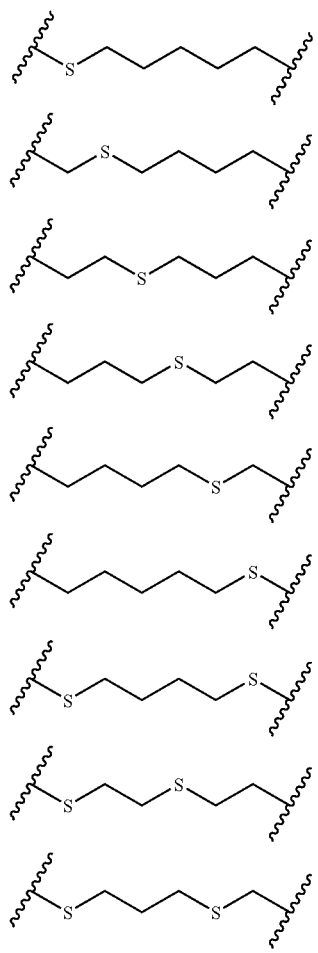

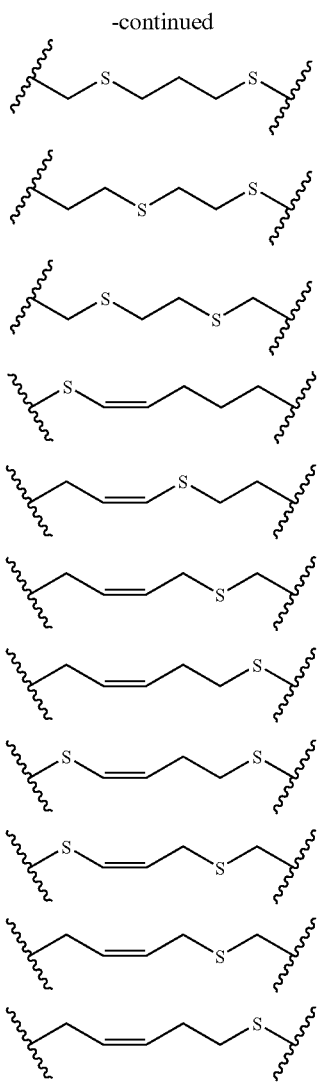

Alternatively, while not intending to limit the scope of the invention in any way, A may be a moiety where O replaces one or two carbon atoms such as one of the following or the like.

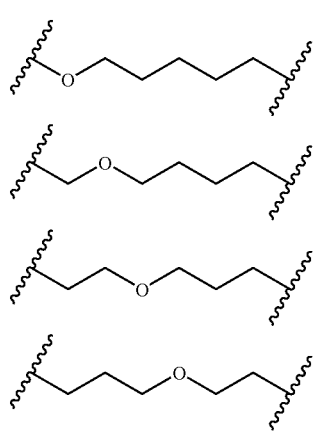

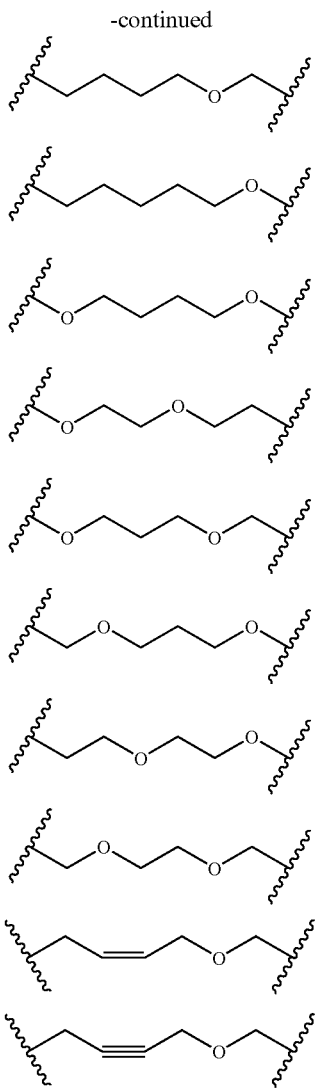

Alternatively, while not intending to limit the scope of the invention in any way, A may have an O replacing one carbon atom and an S replacing another carbon atom, such as one of the following or the like.

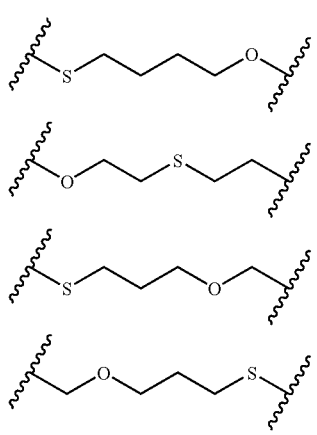

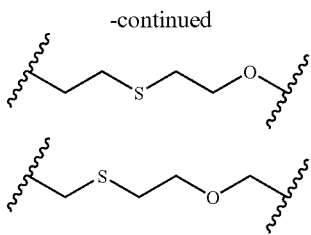

Alternatively, while not intending to limit the scope of the invention in any way, in certain embodiments A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O. In other words, while not intending to limit the scope of the invention in any way, in one embodiment A comprises from 1 to 4 CH$_2$ moieties and Ar, e.g. —CH$_2$—Ar—, —(CH$_2$)$_2$—Ar—, —CH$_2$—ArCH$_2$—, —CH$_2$Ar(CH$_2$)$_2$—, —(CH$_2$)$_2$—Ar(CH$_2$)$_2$—, and the like; or A comprises O, from 0 to 3 CH$_2$ moieties, and Ar, e.g., —O—Ar—, Ar—CH$_2$—O—, —O—Ar—(CH$_2$)$_2$—, —O—CH$_2$—Ar—, —O—CH$_2$—Ar—(CH$_2$)$_2$, and the like; or A comprises S, from 0 to 3 CH$_2$ moieties, and Ar, e.g., —S—Ar—, Ar—CH$_2$—S—, —S—Ar—(CH$_2$)$_2$—, —S—CH$_2$—Ar—, —S—CH$_2$—Ar—(CH$_2$)$_2$, —CH$_2$—CH$_2$—S—Ar—, and the like.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substitutuents in addition to the two parts of the molecule it connects.

In one embodiment, Ar is substituted or unsubstituted interphenylene, interthienylene, interfurylene, or interpyridinylene. In another embodiment Ar is interphenylene (Ph). In another embodiment A is —(CH$_2$)$_2$-Ph-. While not intending to limit scope of the invention in any way, substituents may have 4 or less heavy atoms, or in other words, non hydrogen atoms. Any number of hydrogen atoms required for a particular substituent will also be included. Thus, the substituent may be hydrocarbyl having up to 4 carbon atoms, including alkyl up to C$_4$, alkenyl, alkynyl, and the like;

hydrocarbyloxy up to C$_3$;

CF$_3$;

halo, such as F, Cl, or Br;

hydroxyl;

NH$_2$ and alkylamine functional groups up to C$_3$;

other N or S containing substituents;

and the like.

In one embodiment A is —(CH$_2$)$_m$—Ar—(CH$_2$)$_o$— wherein Ar is interphenylene, the sum of m and o is from 1 to 3, and wherein one CH$_2$ may be substituted with S or O.

In another embodiment A is —CH$_2$—Ar—OCH$_2$—. In another embodiment A is —CH$_2$—Ar—OCH$_2$— and Ar is interphenylene. In another embodiment, Ar is attached at the 1 and 3 positions, such as when A has the structure shown below.

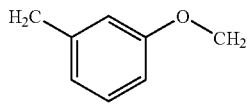

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_2$-Ph- wherein one CH$_2$ may be substituted with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_2$-Ph-.

B is C=O, CH$_2$, CHOH, CHCl, CHF, CHBr or CHCN. Thus, while not intending to limit the scope of the invention in any way, compounds such as those described by the structural formulas below, or pharmaceutically acceptable salts thereof, are possible.

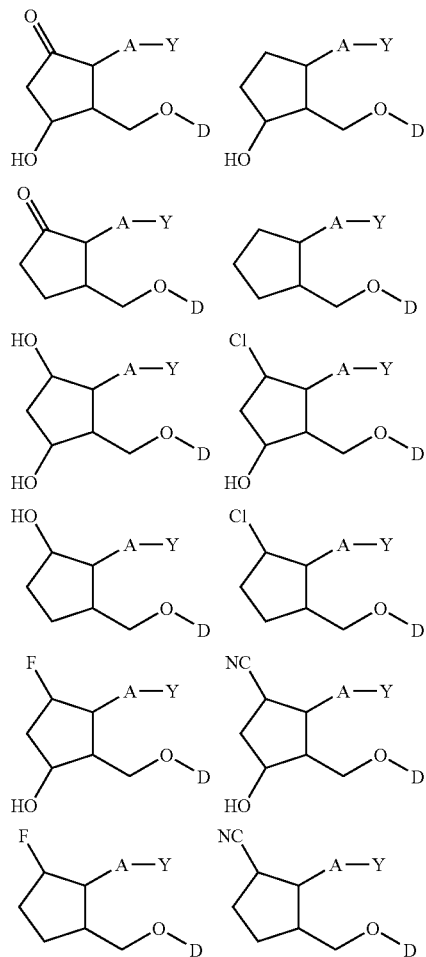

-continued

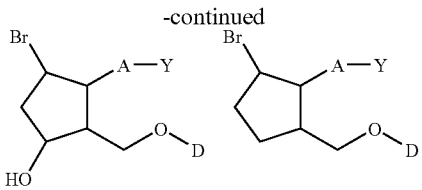

In one embodiment B is CH$_2$, CHOH, CHCl, CHF, CHBr, or CHCN.

In another embodiment B is C=O, CH$_2$, CHCl, CHF, CHBr, or CHCN.

In another embodiment B is C=O.
In another embodiment B is CH$_2$.
In another embodiment B is CHOH.
In another embodiment B is CHCl.
In another embodiment B is CHF.
In another embodiment B is CHCN.
In another embodiment B is CHBr.
G is OH or H.
In one embodiment G is OH.
In another embodiment G is H.

Thus, while not intending to limit the scope of the invention in any way, compounds such as those described by the structural formulas below, or pharmaceutically acceptable salts thereof, are possible.

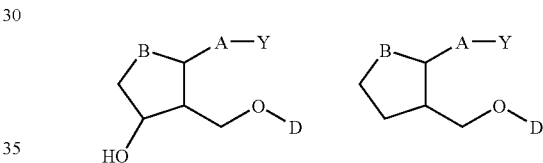

D is aryl or heteroaryl.

Aryl is an unsubstituted or substituted aromatic ring or ring system such as phenyl, naphthyl, biphenyl, and the like.

Heteroaryl is aryl having one or more N, O, or S atoms in the ring, i.e. a ring carbon is substituted by N, O, or S. While not intending to be limiting, examples of heteroaryl include unsubstituted or substituted thienyl, pyridinyl, furyl, benzothienyl, benzofuryl, imidizololyl, indolyl, and the like.

The substituents of aryl or heteroaryl may have up to 12 non-hydrogen atoms each and as many hydrogen atoms as necessary. Thus, while not intending to limit the scope of the invention in any way, the substituents may be:

hydrocarbyl, such as alkyl, alkenyl, alkynyl, and the like, including linear, branched or cyclic hydrocarbyl, and combinations thereof;

hydrocarbyloxy, meaning O-hydrocarbyl such as OCH$_3$, OCH$_2$CH$_3$, O-cyclohexyl, etc, up to 11 carbon atoms;

hydroxyhydrocarbyl, meaning hydrocarbyl-OH such as CH$_2$OH, C(CH$_3$)$_2$OH, etc, up to 11 carbon atoms;

nitrogen substituents such as NO$_2$, CN, and the like, including amino, such as NH$_2$, NH(CH$_2$CH$_3$OH), NHCH$_3$, and the like up to 11 carbon atoms;

carbonyl substituents, such as CO$_2$H, ester, amide, and the like;

halogen, such as chloro, fluoro, bromo, and the like fluorocarbyl, such as CF$_3$, CF$_2$CF$_3$, etc.;

phosphorous substituents, such as $PO_3^{2-}$, and the like;

sulfur substituents, including S-hydrocarbyl, SH, $SO_3H$, $SO_2$-hydrocarbyl, $SO_3$-hydrocarbyl, and the like.

In certain embodiments, the number of non-hydrogen atoms is 6 or less in a substituent. In other embodiments, the number of non-hydrogen atoms is 3 or less in a substituent. In other embodiments, the number of non-hydrogen atoms on a substituent is 1.

In certain embodiments, the substituents contain only hydrogen, carbon, oxygen, halogen, nitrogen, and sulfur. In other embodiments, the substituents contain only hydrogen, carbon, oxygen, and halogen.

Unless otherwise indicated, references to aryl, heteroaryl, phenyl, thienyl, benzothienyl, and the like are intended to mean both the substituted and the unsubstituted moiety.

Thus, compounds wherein D is any of the above classes or species of aryl or heteroaryl are contemplated herein.

Further, while not intending to limit the scope of the invention in any way, in one embodiment D is phenyl. In another embodiment D is chlorophenyl, meaning phenyl with one or more chloro substituents. In another embodiment D is 3,5-dichlorophenyl. In another embodiment D is unsubstituted phenyl.

One embodiment comprises

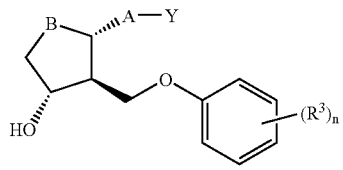

or a pharmaceutically acceptable salt thereof;

wherein A and Y are as described herein;

B is CHCl, CHF, or $CH_2$;

$R^3$ is independently methyl, ethyl, isopropyl, fluoro, chloro, bromo, methoxy, ethoxy, isopropoxy, $NH_2$, OH, CN, $NO_2$, or $CF_3$; and n is from 0 to 3.

Another embodiment comprises

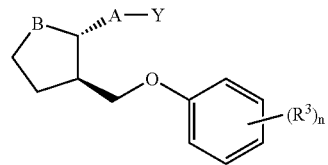

or a pharmaceutically acceptable salt thereof;

wherein A and Y are as described herein;

B is CHCl, CHF, or $CH_2$;

$R^3$ is independently methyl, ethyl, isopropyl, fluoro, chloro, bromo, methoxy, ethoxy, isopropoxy, $NH_2$, OH, CN, $NO_2$, or $CF_3$; and n is from 0 to 3.

Another embodiment comprises

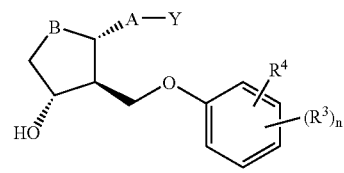

or a pharmaceutically acceptable salt thereof;

wherein A and Y are as described herein;

B is CHCl, CHF, or $CH_2$;

$R^3$ is independently methyl, ethyl, isopropyl, fluoro, chloro, bromo, methoxy, ethoxy, isopropoxy, $NH_2$, OH, CN, $NO_2$, or $CF_3$;

$R^4$ is hydroxyhydrocarbyl having from 1 to 10 carbon atoms; and n is from 0 to 3.

Other embodiments comprise compounds according to the structures below, or pharmaceutically acceptable salts thereof. In these embodiments A is as described herein;

B is either C=O, $CH_2$, CHOH, CHCl, CHF, or CHCN, or alternatively B is CHCl, CHF, or $CH_2$; and Y, $R^3$ and n are as described herein.

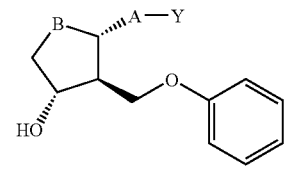

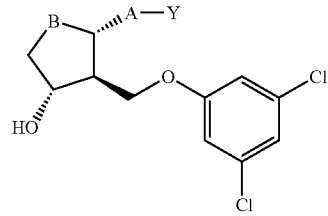

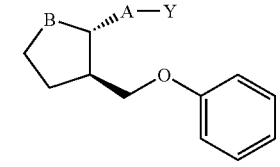

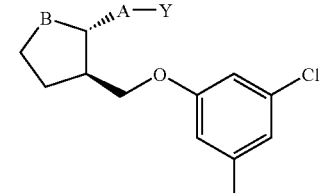

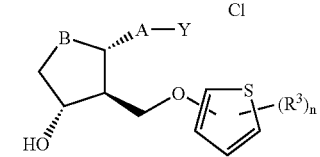

-continued

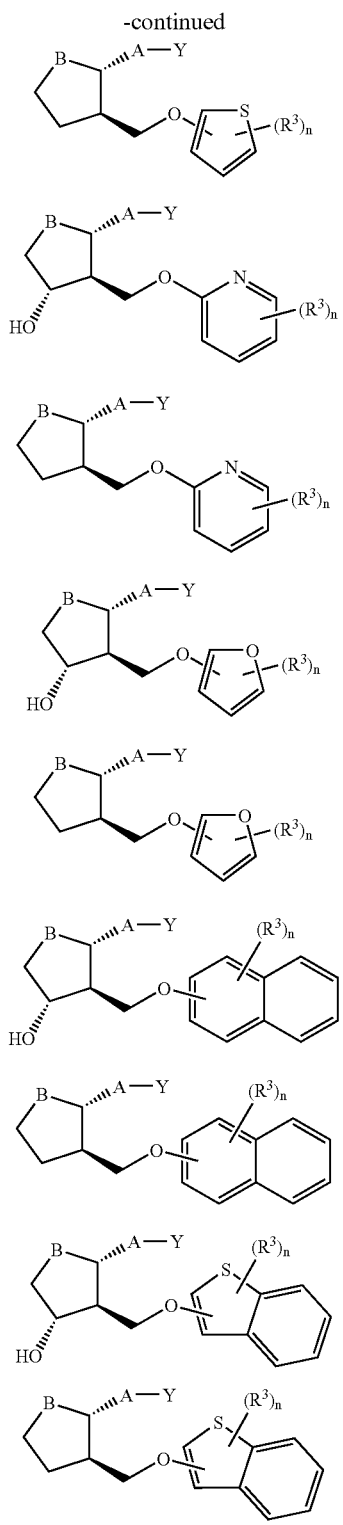

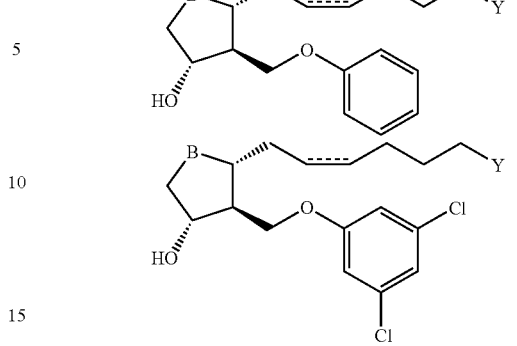

Pharmaceutically acceptable salts of the above listed compounds are also contemplated.

The compounds of disclosed herein are useful for the prevention or treatment of glaucoma or ocular hypertension in mammals, or for the manufacture of a medicament for the treatment of glaucoma or ocular hypertension.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Other embodiments comprise compounds according to the structures below, or pharmaceutically acceptable salts thereof. In these embodiments B is either C=O, $CH_2$, CHOH, CHCl, CHF, or CHCN, or alternatively B is CHCl, CHF, or $CH_2$; and Y, $R^3$ and n are as described herein.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjuster | 1-10 |
| buffer | 0.01-10 |
| pH adjuster | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

Synthetic Methods

The compound disclosed herein are prepared from compounds according to the structure below, which may be obtained using procedures disclosed in U.S. Provisional Patent Application No. 60/644,069, filed on Jan. 14, 2005; U.S. Provisional Patent Application No. 60/757,696, filed on Jan. 10, 2006; and WO2006076370. The parts of these documents disclosing synthesis of the compounds therein are incorporated herein by reference.

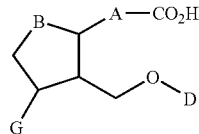

Scheme 1

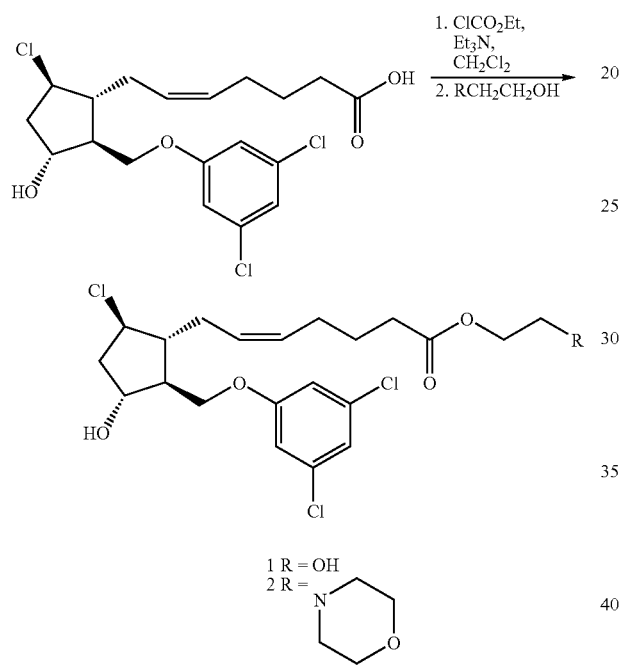

1 R = OH
2 R = <morpholinyl group>

(Z)-7-[(1R,2S,3R,5R)-5-Chloro-2-(3,5-dichloro-phenoxymethyl)-3-hydroxy-cyclopentyl]-hept-5-enoic acid 2-hydroxy-ethyl ester (1)

Triethylamine (15 μL, 0.11 mmol) and ethyl chloroformate (15 μL, 0.16 mmol) were added sequentially to a solution of (Z)-7-[(1R,2S,3R,5R)-5-chloro-2-(3,5-dichloro-phenoxymethyl)-3-hydroxy-cyclopentyl]-hept-5-enoic acid (U.S. Provisional Patent Application No. 60/644,069, filed on Jan. 14, 2005, incorporated by reference herein, 10.5 mg, 0.025 mmol) in $CH_2Cl_2$ (0.2 mL) at room temperature. After 2.5 h, triethylamine (15 μL, 0.11 mmol) and ethylene glycol (200 μL, 3.59 mmol) were added. After stirring overnight at room temperature, the reaction mixture was partitioned between $H_2O$ (5 mL) and $CH_2Cl_2$ (5 mL). The phases were separated and the aqueous phase was extracted with $CH_2Cl_2$ (2×5 mL). The combined organic phase was washed with 1 N HCl (5 mL) then dried ($MgSO_4$), filtered and concentrated in vacuo. Purification of the residue by flash column chromatography on silica gel (10% MeOH/$CH_2Cl_2$) afforded 2.5 mg (22%) of the title compound (1).

(Z)-7-[(1R,2S,3R,5R)-5-Chloro-2-(3,5-dichloro-phenoxymethyl)-3-hydroxy-cyclopentyl]-hept-5-enoic acid 2-morpholin-4-yl-ethyl ester (2)

Triethylamine (6.5 μL, 0.047 mmol) and ethyl chloroformate (7 μL, 0.073 mmol) were added sequentially to a solution of (Z)-7-[(1R,2S,3R,5R)-5-chloro-2-(3,5-dichloro-phenoxymethyl)-3-hydroxy-cyclopentyl]-hept-5-enoic acid (see U.S. 60/644,069, 20 mg, 0.047 mmol) in $CH_2Cl_2$ (0.47 mL) at room temperature. After 2.5 h, triethylamine (6.5 μL, 0.047 mmol) and 4-(2-hydroxyethyl)-morpholine (58 μL, 0.47 mmol) were added. After stirring overnight at room temperature, the reaction mixture was partitioned between $H_2O$ (5 mL) and $CH_2Cl_2$ (5 mL). The phases were separated and the aqueous phase was extracted with $CH_2Cl_2$ (2×5 mL). The combined organic phase was washed with 1 N HCl (5 mL) then dried ($MgSO_4$), filtered and concentrated in vacuo. Purification of the residue by flash column chromatography on silica gel (5% MeOH/$CH_2Cl_2$) afforded 5.1 mg (20%) of the title compound (2).

IN VIVO EXAMPLES

<structure 1>

(Z)-7-[(1R,2S,3R,5R)-5-Chloro-2-(3,5-dichloro-phenoxymethyl)-3-hydroxy-cyclopentyl]-hept-5-enoic acid 2-hydroxy-ethyl ester (1) was tested in normotensive dogs at 0.1%, dosing once daily for 5 days. The maximum intraocular pressure (IOP) decrease from baseline was 6.6 mmHg (40%) at 78 h; the maximum ocular surface hyperemia (OSH) score was 0.9 at 50 h. This compound was also tested in laser-induced hypertensive monkeys, using one single day dose. At 0.1%, the maximum IOP decrease from baseline was 12.5 mmHg (33%) at 4

<structure 2>

(Z)-7-[(1R,2S,3R,5R)-5-Chloro-2-(3,5-dichloro-phenoxymethyl)-3-hydroxy-cyclopentyl]-hept-5-enoic acid 2-morpholin-4-yl-ethyl ester (2) was tested in normotensive dogs at 0.1%, dosing once daily for 5 days. The maximum intraocular pressure (IOP) decrease from baseline was 5.1 mmHg (34%) at 78 h; the maximum ocular surface hyperemia (OSH) score was 0.9 at 30 h. This compound was also tested in laser-induced hypertensive monkeys, using one single day dose. At 0.1%, the maximum IOP decrease from baseline was 11.9 mmHg (32%) at 6 h.

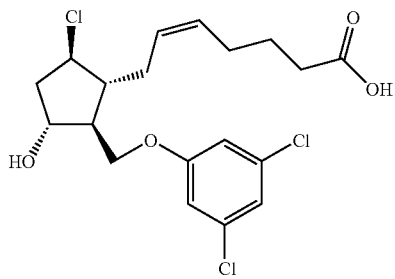

(Z)-7-[(1R,2S,3R,5R)-5-Chloro-2-(3,5-dichloro-phenoxymethyl)-3-hydroxy-cyclopentyl]-hept-5-enoic acid was tested at multiple concentrations in normotensive dogs, dosing once daily for 5 days. At 0.05%, the maximum IOP decrease from baseline was 4.3 mmHg (30%) at 6 h; the maximum OSH score was 0.6 at 6 h. At 0.1%, the maximum IOP decrease from baseline was 4.8 mmHg (34%) at 102 h; the maximum OSH score was 1.3 at 6 h. This compound was also tested in laser-induced hypertensive monkeys, using one single day dose. At 0.1%, the maximum IOP decrease from baseline was 6 mmHg (19%) at 6 h.

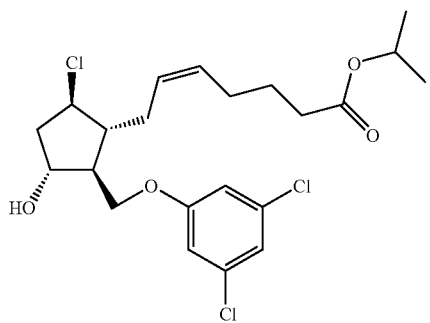

(Z)-7-[(1R,2S,3R,5R)-5-Chloro-2-(3,5-dichloro-phenoxymethyl)-3-hydroxy-cyclopentyl]-hept-5-enoic acid isopropyl ester was tested at multiple concentrations in normotensive dogs, dosing once daily for 5 days. At 0.01%, the maximum intraocular pressure (IOP) decrease from baseline was 1.1 mmHg (7%) at 2 h; the maximum ocular surface hyperemia (OSH) score was 0.6 at 74 h. At 0.05%, the maximum intraocular pressure (IOP) decrease from baseline was 2.8 mmHg (18%) at 6 h; the maximum ocular surface hyperemia (OSH) score was 0.6 at 74 h. This compound was also tested in laser-induced hypertensive monkeys, using one single day dose. At 0.01%, the maximum IOP decrease from baseline was 6.8 mmHg (18%) at 6 h. At 0.05%, the maximum IOP decrease from baseline was 6 mmHg (16%) at 2 h.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:
1. A compound of the formula

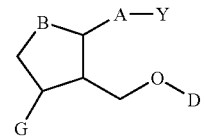

or a pharmaceutically acceptable salt thereof;
wherein Y is
—$CO_2(CH_2)_2OH$ or

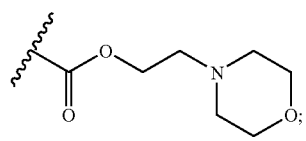

A is —$(CH_2)_6$—, cis —$CH_2CH=CH$—$(CH_2)_3$—, or —$CH_2C\equiv C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O;
B is C=O, $CH_2$, CHOH, CHCl, CHF, CHBr, or CHCN;
G is OH or H; and
D is aryl or heteroaryl.
2. The compound of claim 1 wherein D is phenyl.
3. The compound of claim 2 wherein D is chlorophenyl.
4. The compound of claim 3 wherein D is 3,5-dichlorophenyl.
5. The compound of claim 2 wherein D is unsubstituted phenyl.
6. The compound of claim 1 wherein A is —$(CH_2)_6$—, cis —$CH_2CH=CH$—$(CH_2)_3$—, or —$CH_2C\equiv C$—$(CH_2)_3$—.
7. The compound of claim 1 wherein B is C=O.
8. The compound of claim 1 wherein B is CHCl.
9. The compound of claim 2 having the formula

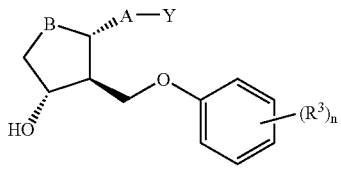

or a pharmaceutically acceptable salt thereof;
wherein B is CHCl, CHF, or $CH_2$;
$R^3$ is independently methyl, ethyl, isopropyl, fluoro, chloro, bromo, methoxy, ethoxy, isopropoxy, $NH_2$, OH, CN, $NO_2$, or $CF_3$; and
n is from 0 to 3.

10. The compound of claim 9 having the formula

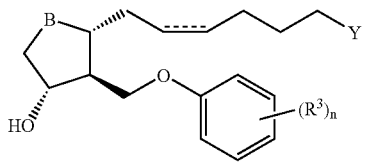

or a pharmaceutically acceptable salt thereof;
wherein a dashed line indicates the presence or absence of a covalent bond.

11. The compound of claim 1 wherein B is $CH_2$, CHOH, CHCl, CHF, CHBr, or CHCN.

12. The compound of claim 11 wherein B is $CH_2$.

13. The compound of claim 8 having the formula

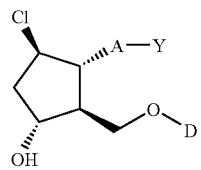

or a pharmaceutically acceptable salt thereof
wherein D is substituted phenyl.

14. The compound of claim 13 having the formula

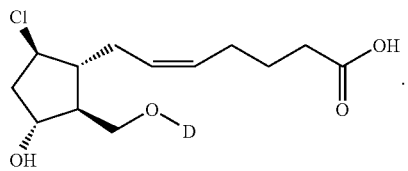

15. The compound of claim 2 having the formula

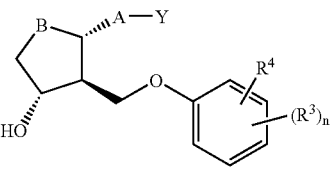

or a pharmaceutically acceptable salt thereof;
wherein B is CHCl, CHF, or $CH_2$;
$R^3$ is independently methyl, ethyl, isopropyl, fluoro, chloro, bromo, methoxy, ethoxy, isopropoxy, $NH_2$, OH, CN, $NO_2$, or $CF_3$;
$R^4$ is hydroxyhydrocarbyl having from 1 to 10 carbon atoms; and
n is from 0 to 3.

16. The compound of claim 1 wherein G is H.

17. The compound of claim 1 selected from
(Z)-7-[(1R,2S,3R,5R)-5-Chloro-2-(3,5-dichloro-phenoxymethyl)-3-hydroxy-cyclopentyl]-hept-5-enoic acid 2-hydroxy-ethyl ester; and
(Z)-7-[(1R,2S,3R,5R)-5-Chloro-2-(3,5-dichloro-phenoxymethyl)-3-hydroxy-cyclopentyl]-hept-5-enoic acid 2-morpholin-4-yl-ethyl ester.

18. A composition comprising a compound having a structure according to any one of claims 1 to 17, said composition being a liquid which is ophthalmically acceptable.

19. A method of treating glaucoma or ocular hypertension comprising administering a compound according to any one of claims 1 to 17 to a mammal in need thereof.

* * * * *